US00PP10842P

United States Patent [19]

Bolwijn

[11] Patent Number: Plant 10,842

[45] Date of Patent: Mar. 30, 1999

[54] LEUCOTHOE AXILLARIS PLANT NAMED 'LIPSBOLWI'

[75] Inventor: A. L. Ch. Bolwijn, Putten, Netherlands

[73] Assignee: Pride of Place Plants Inc., Sidney, Canada

[21] Appl. No.: 989,601

[22] Filed: Dec. 12, 1997

[51] Int. Cl.[6] ..... A01H 5/00

[52] U.S. Cl. ..... Plt./54.1

[58] Field of Search ..... Plt./54.1

*Primary Examiner*—Elizabeth Kemmerer
*Attorney, Agent, or Firm*—Christie, Parker & Hale, LLP

[57] ABSTRACT

An axillaris plant variety having dark purple, glossy foliage in winter and compact growth habit.

1 Drawing Sheet

BACKGROUND OF THE INVENTION

The present invention relates to a new and distinct variety of Leucothoe axillaris which was discovered as a natural mutation in a controlled planting of the variety Leucothoe axillaris 'Scarletta'. The varietal denomination of this new plant variety is 'Lipsbolwi'.

SUMMARY OF THE INVENTION

Among the novel characteristics possessed by the new variety which distinguish it from its parent and all other varieties of which I am aware are its attractive glossy, dark purple foliage through winter and compact growth habit.

Asexual reproduction by vegetative cuttings of the new variety as performed in The Netherlands shows that the foregoing and other distinguishing characteristics come true to form and are established and transmitted through succeeding propagations. Other known forms of asexual reproduction may be also used.

COMPARISON WITH PARENT

The new variety, differs from its parent 'Scarletta' in producing a smaller plant that grows more compact. The leaves of 'Lipsbolwi' are smaller and narrower and much darker than the parent.

BRIEF DESCRIPTION OF ILLUSTRATION

The accompanying illustration shows a typical specimen of the vegetative growth of the new variety depicted in color as nearly true as it is reasonably possible to make the same in a color illustration of this character.

DESCRIPTION OF THE NEW VARIETY

Parentage: Mutation.
Parent: Axillaris 'Scarletta'.
Class: Axillaris.

The following is a detailed description of the new variety, from specimens grown outdoors inn The Netherlands. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Plant

A. Form: Compact, mounded habit.
B. Growth: Extremely uniform; attains heights of about 25 cm.
C. Foliage:
  (1) *Size.*—About 10 cm×2 cm, single simple leaves.
  (2) *Quantity.*—Abundant; dense and overlapping.
  (3) *Color.*—New foliage: Upper side—some leaves are red, near 180A, to 183A or red/green; underside—grey green. Old foliage: Upper side near 136A to 138A and dark brown, red purple, near 183A, in winter; underside somewhat lighter in color.
  (4) *Shape.*—Narrowly elliptic, acute.
  (5) *Texture.*—Upper side glossy, leather-like texture; underside dull, leathery.
  (6) *Edge.*—Serrated, serrulate.
  (7) *Serration (type).*—Irregular, rounded and often remote serration.
  (8) *Petiole.*—Color similar to leaves.
  (9) *Veination.*—Very small.
  (10) *Resistance to disease.*—No disease to date.
D. Wood:
  (1) *New shoots.*—Red/green, bark smooth.
  (2) *Old wood.*—Summer—green; winter-red/brown; bark smooth.
E. Winter hardiness: Winter hardy in The Netherlands when planted.

Flowers

Typical ericaceous flowers; white to pink urceolate; inflorenscence up to about 6 cm in length held just above foliage.

Reproductive Organs

A. Stamens: About 10 filaments and anthers, regularly arranged around style.
  (1) *Color.*—Filaments—white/cream; anthers—yellow.
B. Pollen: Yellow, viscid.
C. Styles: Exceeding anthers.
D. Stigmas Capitate, white/cream color.

I claim:

1. A new and distinct axillaris plant variety, substantially as shown and described.

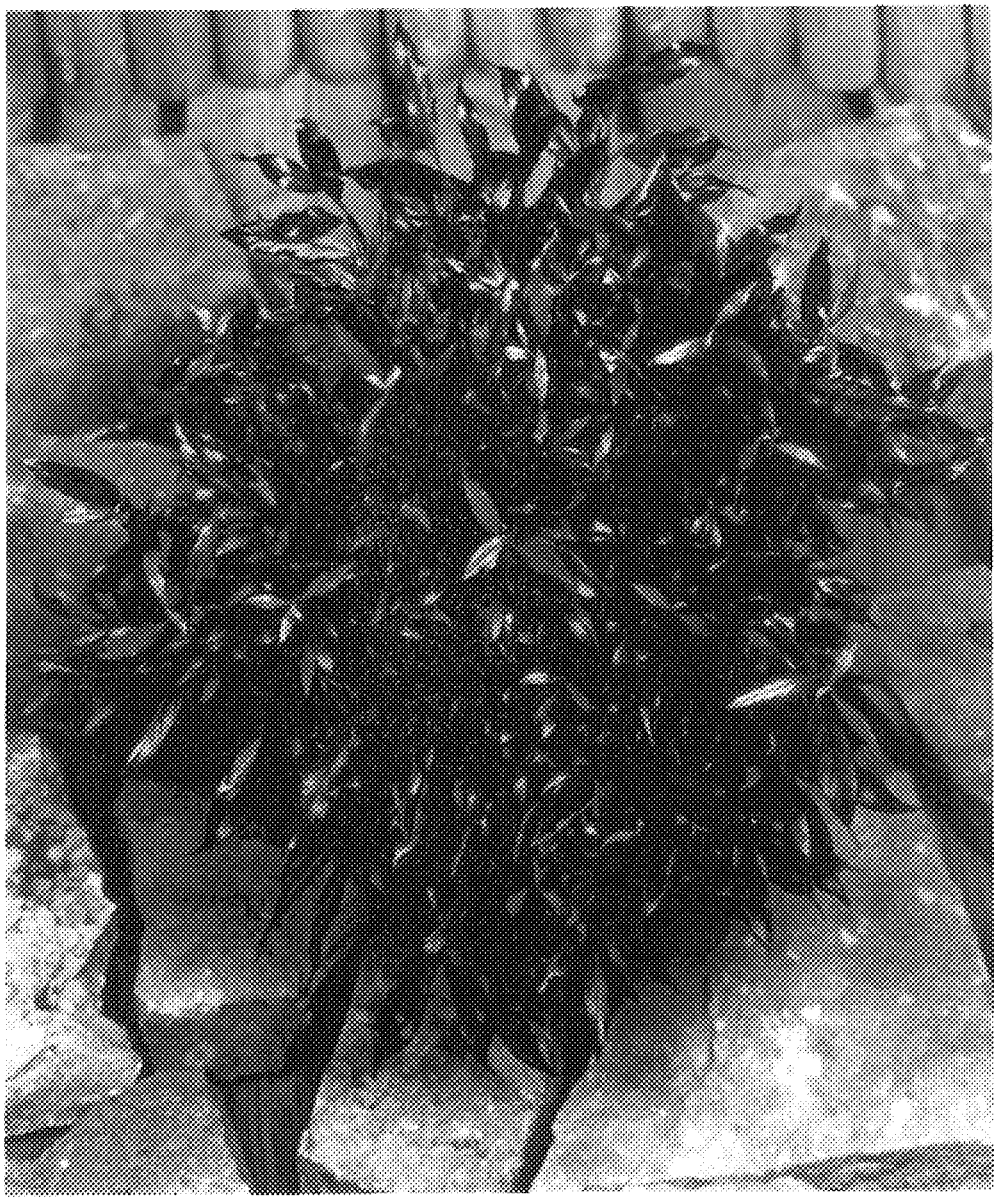

* * * * *